(12) United States Patent
Chartrand et al.

(10) Patent No.: US 10,688,242 B2
(45) Date of Patent: Jun. 23, 2020

(54) HIGH FLOW RATE DUAL RESERVOIR PORT SYSTEM

(71) Applicant: AngioDynamics, Inc., Latham, NY (US)

(72) Inventors: Bradley D. Chartrand, Saratoga Springs, NY (US); Raymond Lareau, Westford, MA (US); Daniel Buehner, Queensbury, NY (US); Tobin Kovoor, Rye Brook, NY (US); Brian Nentwick, Greenfield Center, NY (US)

(73) Assignee: AngioDynamics, Inc., Latham, NY (US)

(*) Notice: Subject to any disclaimer, the term of this patent is extended or adjusted under 35 U.S.C. 154(b) by 0 days.

(21) Appl. No.: 15/618,522

(22) Filed: Aug. 18, 2017

(65) Prior Publication Data

US 2018/0369475 A1 Dec. 27, 2018

Related U.S. Application Data

(63) Continuation of application No. 13/852,436, filed on Mar. 28, 2013, now Pat. No. 9,707,339.

(51) Int. Cl.
*A61M 5/142* (2006.01)
*A61M 1/36* (2006.01)
*A61M 39/02* (2006.01)

(52) U.S. Cl.
CPC ...... *A61M 5/14276* (2013.01); *A61M 1/3659* (2014.02); *A61M 1/3661* (2014.02); *A61M 2039/0211* (2013.01); *A61M 2205/04* (2013.01)

(58) Field of Classification Search
CPC .............. A61M 1/3659; A61M 1/3661; A61M 2039/0211; A61M 2205/04; A61M 5/14276; A61M 39/0208
See application file for complete search history.

(56) References Cited

U.S. PATENT DOCUMENTS

| | | | | |
|---|---|---|---|---|
| 4,692,146 A | * | 9/1987 | Hilger | A61M 39/0208 604/173 |
| 4,892,518 A | * | 1/1990 | Cupp | A61M 39/0208 137/855 |
| 5,085,644 A | * | 2/1992 | Watson | A61M 5/1428 604/153 |
| 5,160,325 A | * | 11/1992 | Nichols | A61M 25/003 604/247 |
| 5,171,305 A | * | 12/1992 | Schickling | A61M 25/0119 604/271 |
| 5,792,104 A | * | 8/1998 | Speckman | A61M 39/0208 604/175 |
| 5,944,688 A | * | 8/1999 | Lois | A61M 39/0208 604/175 |
| 5,951,512 A | * | 9/1999 | Dalton | A61M 39/0208 604/175 |

(Continued)

*Primary Examiner* — Quynh-Nhu H. Vu
(74) *Attorney, Agent, or Firm* — Peter Flora (57) ABSTRACT

Devices and methods for obtaining high flow rates in a port catheter system, and devices and methods for using a high flow rate port catheter system are disclosed. In one embodiment, a reservoir is dedicated for aspiration and a separate reservoir is dedicated for infusion. Fluid flow channels associated with aspiration are larger than the fluid flow channels associated with infusion. The catheter connected to the port can have an offset tip configuration. Methods for accessing the port are also disclosed.

4 Claims, 8 Drawing Sheets

(56) References Cited

U.S. PATENT DOCUMENTS

| | | | | |
|---|---|---|---|---|
| 6,022,335 | A * | 2/2000 | Ramadan | A61M 39/0208 |
| | | | | 604/175 |
| 6,132,416 | A * | 10/2000 | Broselow | A61J 1/1425 |
| | | | | 128/898 |
| 6,562,023 | B1 * | 5/2003 | Marrs | A61M 39/0208 |
| | | | | 604/288.01 |
| 8,267,915 | B2 * | 9/2012 | Daly | A61M 39/0208 |
| | | | | 604/288.01 |
| 9,707,339 | B2 * | 7/2017 | Chartrand | A61M 1/3659 |
| 2004/0167463 | A1 * | 8/2004 | Zawacki | A61M 25/0026 |
| | | | | 604/43 |
| 2005/0124980 | A1 * | 6/2005 | Sanders | A61M 39/0208 |
| | | | | 604/891.1 |
| 2008/0294111 | A1 * | 11/2008 | Tal | A61M 25/0097 |
| | | | | 604/165.01 |
| 2010/0049147 | A1 * | 2/2010 | Tanikawa | A61B 17/22 |
| | | | | 604/265 |
| 2011/0264058 | A1 * | 10/2011 | Linden | A61M 39/02 |
| | | | | 604/288.01 |

* cited by examiner

HIGH FLOW RATE DUAL RESERVOIR PORT SYSTEM

CROSS-REFERENCE TO RELATED APPLICATIONS

This application claims priority to U.S. provisional application No. 61/616,675 filed on Mar. 28, 2012, and U.S. provisional application No. 61/617,219 filed on Mar. 29, 2012, both of which are incorporated herein by reference in their entireties.

FIELD OF THE INVENTION

The present invention relates generally to implantable port systems. More specifically, the invention relates to port catheter systems optimized for high flow rates, patient comfort, and minimization of recirculation during procedures requiring the extracorporeal treatment of blood.

BACKGROUND OF THE INVENTION

Multi-lumen catheters are commonly used for procedures requiring access to the vascular system and the extracorporeal treatment of blood. Procedures may include for example apheresis or hemodialysis. During these types of procedures, blood is aspirated from the vascular system, treated and returned to the vascular system through an infusion lumen. Treatments might include for example a blood component separation process, where only certain blood components are returned to the body, or a blood filtering process, where blood is continuously filtered through a closed loop circuit.

Medical professionals often prefer the use of implantable ports for accessing the vascular system since they are completely indwelling. Implantable ports may be advantageous over catheters since ports are hidden from view, are often more desirable for patients with active lifestyles, and can minimize the risk for infection, especially in patients that require more chronic care. Ports are typically implanted in the chest and connected to a catheter having a tip positioned at the point of treatment. The catheter tip is most commonly positioned at the junction of the superior vena cava and the right atrium. Ports can have one or more reservoirs in fluid communication with one or more lumens of the catheter. A needle-penetrable and self-sealing septum covers the reservoir, and the reservoir can be accessed with a needle. The needle can be used for infusing or aspirating fluid to and from the tip of the catheter.

Multi-reservoir port systems are generally known, and often used in practice for procedures where it is desirable to have multi-reservoir and multi-lumen access to the vascular system. Procedures may, for example, require the administration of different fluids through separate reservoirs, or an administration of fluid through one reservoir and aspiration through a separate reservoir. However, for high flow rate procedures utilizing conventional port systems, specifically those procedures automated by machine for powering aspiration and infusion, pressure alarms are commonly set-off, warning of high intraluminal pressures in the device that could potentially injure the patient. Further, these conventional multi-reservoir systems tend to be bulky, adding to the discomfort of the patient. An additional downfall of conventional multi-reservoir designs is that they are provided with catheters having distal openings terminating at the same point along the catheter shaft. These conventional port catheter designs would be inefficient for a high flow rate procedure since this catheter tip configuration would lead to high blood recirculation rates. It is therefore desirable to have an improved performance multi-reservoir port system that can optimize flow dynamics to support high flow applications.

SUMMARY OF THE INVENTION

The invention provides, in one aspect, a port catheter system including a port having a first reservoir having a first opening fluidly sealed by a first elastomeric septum, the first reservoir in fluid communication with a first outlet lumen, and a second reservoir having a second opening fluidly sealed by a second elastomeric septum, the second reservoir in fluid communication with a second outlet lumen. A first volume of the first reservoir is larger than a second volume of the second reservoir, and a first cross-sectional area of a first outlet lumen is greater than a second cross-sectional area of the second outlet lumen. The system also includes a catheter having a catheter shaft having a first catheter lumen and a second catheter lumen, the first catheter lumen extending between a first catheter lumen proximal opening and a first catheter lumen distal opening, and the second catheter lumen extending between a second catheter lumen proximal opening and a second catheter lumen distal opening. The first catheter lumen has a greater cross-sectional area than the second catheter lumen, and the first catheter lumen distal opening terminates offset from the second catheter lumen distal opening.

In another aspect, the invention is a port including a first reservoir having a first opening fluidly sealed by a first elastomeric septum, the first reservoir in fluid communication with a first outlet lumen, and a second reservoir having a second opening fluidly sealed by a second elastomeric septum, the second reservoir in fluid communication with a second outlet lumen. A first volume of the first reservoir is larger than a second volume of the second reservoir, and wherein a first cross-sectional area of a first outlet lumen is greater than a second cross-sectional area of the second outlet lumen.

In yet another aspect, the invention is a device for and method of accessing the port, and determining proper access to a port reservoir.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a multi-reservoir port system for the extracorporeal treatment of blood.

Figure 1:
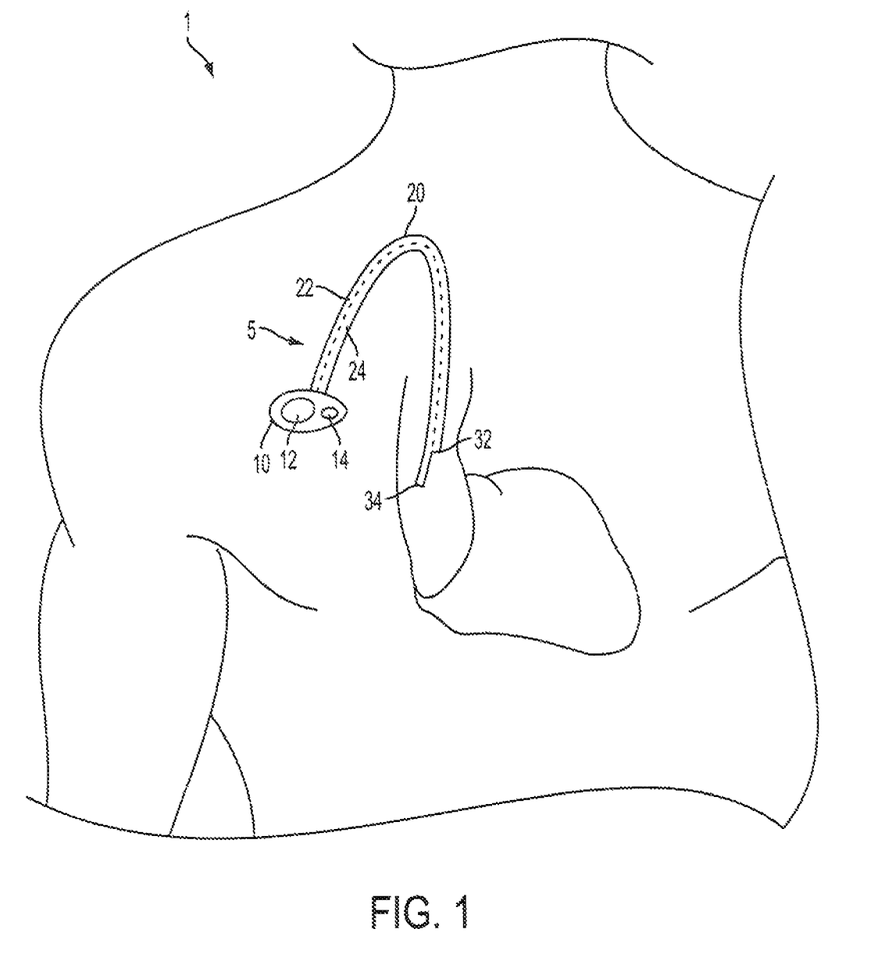
FIG. 1 is a view of a port catheter system implanted in a human according to embodiments of the invention.

As shown in FIG. 1, a port catheter system 5 according to an embodiment of the present invention is implanted subcutaneously in the chest of a human body 1. The system includes a port 10 and a catheter 20. The port 10 has two reservoirs 12, 14 each situated directly beneath a needle-penetrable septum. One reservoir 12 is designated for aspiration, and is in fluid communication with a catheter lumen 22 also designated for aspiration. The other reservoir 14 is designated for infusion, and is in fluid communication with a catheter lumen 24 designated for infusion. The aspiration lumen 22 terminates in an aspiration lumen distal opening 32, and the infusion lumen 24 terminate in an infusion lumen distal opening 34. When implanted, both the aspiration 32 and infusion 34 distal openings are located near the junction of the superior vena cava and the right atrium, which is commonly the target procedure point for extracorporeal blood treatments such as apheresis and hemodialysis. The aspiration lumen distal opening 32 is staggered proximally from the infusion lumen distal opening 34 to minimize recirculation of processed blood.

Figure 2:
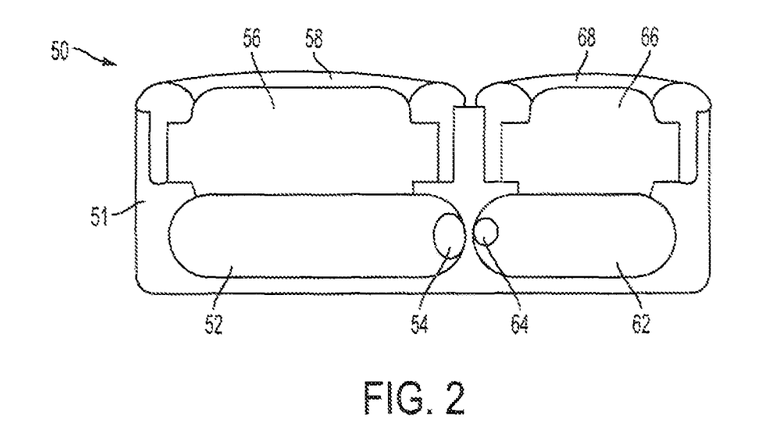
FIG. 2 is a cross-sectional view of a dual reservoir port according to an embodiment of the invention.
Figure 3:
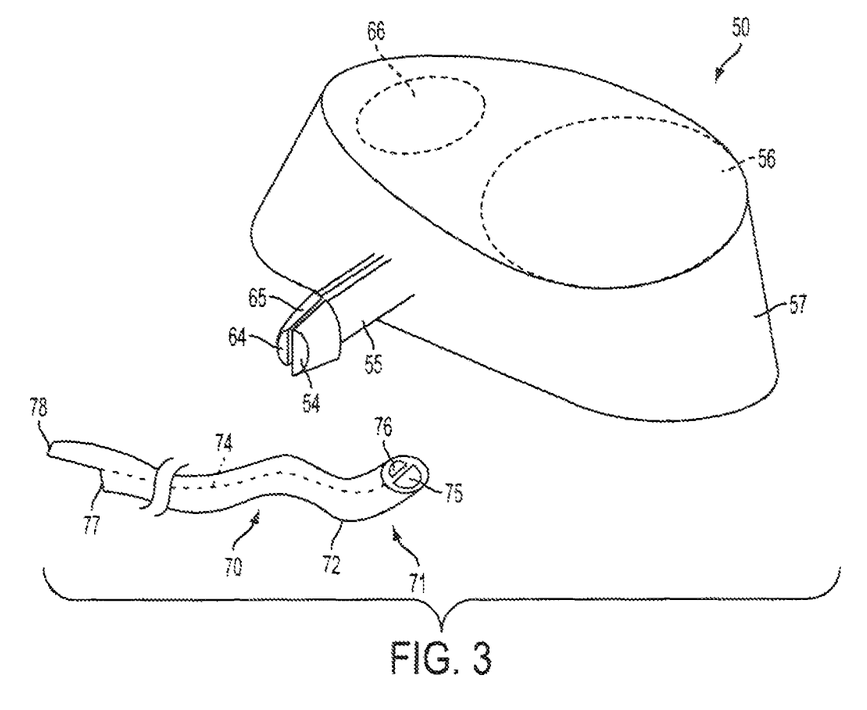
FIG. 3 is a perspective view of a dual reservoir port and a catheter according to the embodiment of the invention shown in FIG. 2.

A more detailed view of a port according to an embodiment of the present invention is shown in FIGS. 2 and 3. The port 50 has a first reservoir 52 in fluid communication with a first outlet lumen 54. The first outlet lumen 54 can be configured at various parts of the reservoir, however, an outlet configured tangentially to a contour reservoir side wall will exhibit superior fluid dynamic characteristics and laminar flow, as described in U.S. Pat. No. 5,951,512, incorporated herein by reference. The first reservoir 52 has contour side walls and its shape is defined by the port body 51. The first reservoir is fluidly sealed at the top by an elastomeric self-sealing septum 56. The septum 56 is secured to the port body 51 by a retaining member 58. Similarly, a second reservoir 62 is in fluid communication with a second outlet lumen 64. The second reservoir 62 is sealed at the top by a septum 66 secured to the port body 51 by a retaining member 68.

As shown in FIG. 2, the first reservoir 52 is larger than the second reservoir 62, and the first outlet lumen 54 is larger than the second outlet lumen 64. As shown in FIG. 3, the corresponding catheter 70 for the port 50 has a proximal end 71 that can be advanced over the outlet stems 55, 65. Each outlet stem 55, 65 defines an outlet lumen 54, 64 for fluid communication between the reservoirs 52, 62 and the catheter lumens 75, 76. The catheter 70 has a shaft 72 and a separating wall 74 for separating fluid communication. The catheter also has a distal aspiration opening 77 and a distal infusion opening 78, the aspiration opening 77 being staggered proximally from the distal infusion opening 78 to minimize recirculation. The aspiration catheter lumen 75 is larger than the infusion catheter lumen 76.

Figure 4:
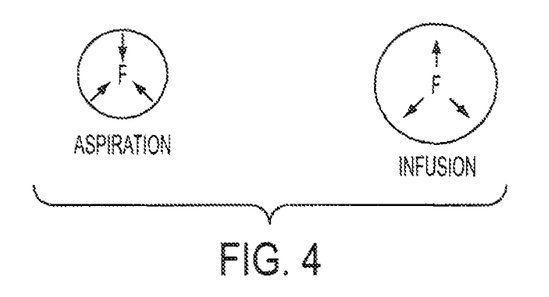
FIG. 4 is a diagram showing the effects of positive and negative luminal pressure forces on the inner cross-sectional area of a flexible lumen side wall.

The design according to the present embodiment provides superior device performance by providing dedicated infusion and aspiration channels for aspiration, upsizing the inner cross-sectional areas of the fluid channels on the aspiration side to accommodate high flow rates without triggering pressure alarms and minimizing risk to the patient. As illustrated in FIG. 4, negative pressure forces within the lumen tend to collapse the flexible catheter wall, shrinking catheter diameter, while positive pressure forces tend to expand the flexible catheter wall. Catheter wall collapse can be especially problematic during initial procedure ramp-up, when a machine is attempting to power aspirate fluid into the reservoir through a mostly empty catheter lumen, lacking the intra-luminal support of a column of fluid. The pressure drop in a fluid flowing in a cylindrical channel can be expressed by the Hagen-Poiseuille equation:

$$\Delta P = \frac{128 \mu L Q}{\pi d^4}$$

A decrease in lumen diameter (d) will cause an increase in pressure drop ($\Delta P$), which could trigger a pressure alarm in the power injection/aspiration machine or harm the patient. This could also interrupt the flow of blood through the circuit, delaying or negatively impacting the effectiveness of the treatment. According to the present embodiment, relative to the infusion channel, a larger luminal cross-section (d) is provided for the aspiration channel, including the aspiration lumen 75, aspiration outlet lumen 54 and aspiration reservoir 52. The larger relative aspiration channel will provide a cross-sectional area adequate for higher flow rates (Q), while keeping the pressure drop (ΔP) at acceptable levels.

Figure 5A:
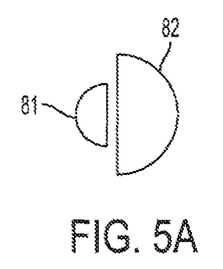
FIG. 5A is a cross-sectional view of opposing D lumens of different sizes.
Figure 5B:
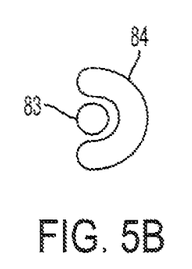
FIG. 5B is a cross-sectional view of a convex lumen paired with a concave lumen.
Figure 5C:
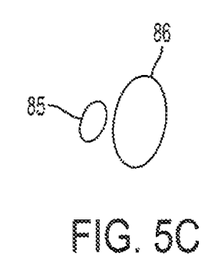
FIG. 5C is a cross-sectional view of two oval lumens of different sizes.

Various cross-sectional lumen configurations can be utilized in the design of the catheter lumens and the port outlet stems, as shown by the examples in FIGS. 5A, 5B, and 5C. An opposing D configuration can be used as shown in FIG. 5A, where the D-shaped lumen 82 dedicated for aspiration is larger than the D-shaped lumen 81 used for infusion. A convex/concave lumen configuration as shown in FIG. 5B can also be utilized such that a convex lumen 83 fits within the contour of a concave lumen 84. Alternatively, two convex lumens 85, 86 of different sizes can be configured adjacent to one another, as shown in FIG. 5C. In another alternative, two concave lumens can be configured adjacent to one another, and to fit within opposing contours. Multi-lumen extrusion techniques known in the art can be used to form the various configurations.

Figures 6A, 6B:
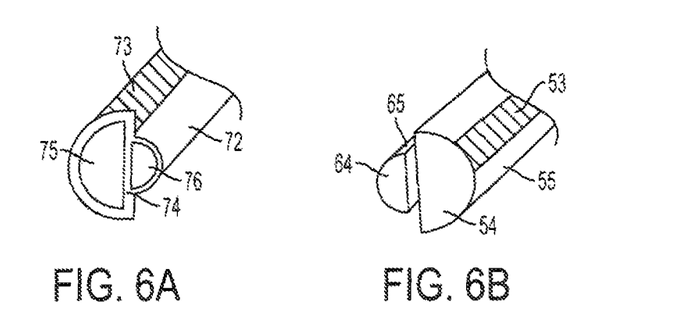
FIG. 6A is a perspective view of the proximal end of a catheter.
FIG. 6B is a perspective view of the distal end of a port stem.

As shown in FIGS. 6A and 6B, corresponding visual markers can be used to indicate to a medical professional which sides of the catheter and outlet stem correspond to one another. This marking system can be helpful when the professional has to connect the proximal end of the catheter to the outlet stem, so that lumens are in fluid communication with the correct reservoir. Corresponding catheter/outlet stem lumens can be properly indicated by matching markers 73, 53, such as the colors red for aspiration and green for infusion, or other means such as alphanumerics or various symbols. The mark can be applied using methods known in the art, such as printing, etching, molding or co-extruding.

Figure 7A:
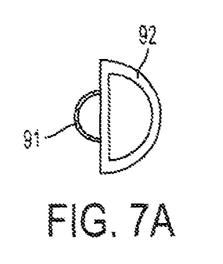
FIG. 7A is a cross-sectional view of lumens having different side wall thicknesses.
Figure 7B:
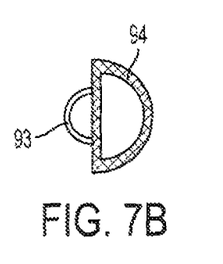
FIG. 7B is a cross-sectional view of a lumen having a reinforcing member in a side wall.
Figure 7C:
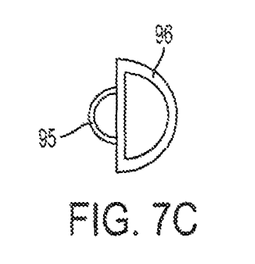
FIG. 7C is a cross-sectional view of lumens having different durometer side walls.

As demonstrated by FIG. 4 and the Hagen-Poiseuille equation, increasing luminal cross-sectional area can keep the pressure drop stable during higher flow rate procedures. As shown in FIGS. 7A, 7B, and 7C, various characteristics of the catheter lumen side walls can be manipulated to facilitate higher luminal cross-sectional areas. Although FIGS. 7A, 7B, and 7C shows a catheter with an irregular outer diameter for illustrative purposes, the outer profile of the catheters can be more rounded or contoured (as shown for example in FIG. 3) without departing from the spirit of the invention. FIG. 7A shows a thin side wall 91 for the infusion lumen and a thick side wall 92 for the aspiration lumen. As demonstrated by the diagram in FIG. 4, the infusion lumen wants to expand under positive pressure force. A thinner infusion side wall 91 manufactured of an elastic polymer can support slight and temporary luminal expansion. Allowing the side wall 91 to obtain a slightly larger luminal cross-sectional area during infusion without permanently deforming the side wall can aid in keeping the pressure drop stable under increasing flow rates. Since this design allows for a relatively smaller infusion lumen, the overall footprint of the port system according to the present invention can be minimized when aspiration and infusion reservoirs are dedicated. Meanwhile, the thicker side wall 92 on the aspiration side resists luminal collapse under negative pressure forces. According to the cross-sectional lumen examples provided in FIGS. 5A, 5B, and 5C, the enlarged aspiration lumen creates a larger overall outer profile for the catheter, and the infusion lumen can be smaller to maintain the overall outer profile. The infusion lumen can therefore be designed to expand slightly and temporarily to create a larger luminal area for infusion without having to increase the overall French size of the catheter. A reinforcing member can also be co-extruded into the aspiration side wall 94 as shown in FIG. 7B. Alternatively, as shown in FIG. 7C, the side wall 96 can be extruded from a higher durometer polymer to resist lumen shrinkage, while the side wall of the infusion side wall 95 can be extruded from a relatively lower durometer polymer to aid lumen expansion.

Figure 8A:
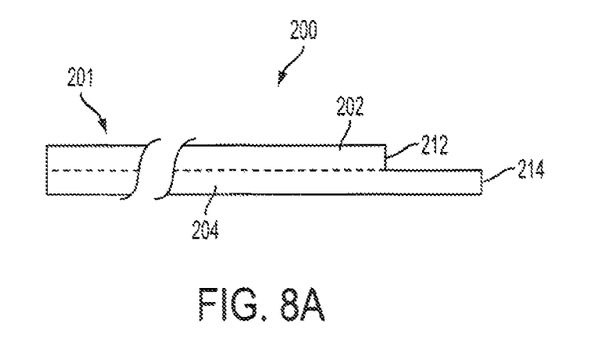
FIG. 8A is a side view of a staggered tip catheter.
Figure 8B:
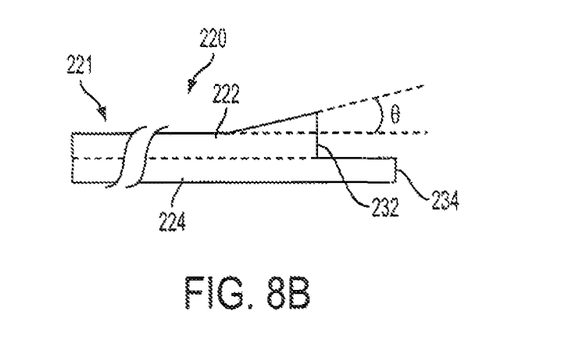
FIG. 8B is a side view of a staggered tip catheter having a flared aspiration lumen opening.

Catheter tip configurations according to the present invention are shown in FIGS. 8A and 8B. A staggered tip configuration as shown in FIG. 8A includes a catheter 200 having an aspiration lumen 202 and an infusion lumen 204. The aspiration lumen 202 can have a larger cross-sectional area than the infusion lumen 204 as described above. The aspiration lumen distal opening 212 and infusion lumen distal opening 214 are both at the distal end of the catheter, and the aspiration lumen distal opening 212 terminates proximal of the infusion lumen distal opening 214 to prevent recirculation. The catheter 200 can be trimmed at its proximal end 201 before it is connected to an outlet stem to customize catheter length. An alternative tip configuration is shown in the catheter 220 of FIG. 8B. The catheter 220 has an aspiration lumen 222, an infusion lumen 224, an aspiration distal lumen opening 232, an infusion lumen distal opening 234, and a trimmable proximal end 221. As mentioned above, catheter wall collapse can be especially problematic during initial procedure ramp-up, when the power aspirator initially supplies negative pressure to an empty aspiration lumen. The aspiration lumen distal opening 232 according to this embodiment features a flared opening which acts as a staging area for blood, so that blood is allowed to pool at the opening during aspiration ramp-up, rapidly presenting higher volumes of fluid within the aspiration lumen for supporting the wall and lessening the likelihood of wall collapse. Similarly, the infusion lumen distal opening 234 can feature a flared opening to redistribute fluid being reintroduced into the body over a larger area, minimizing potentially harmful side effects of high flow rate infusions.

Figure 9:
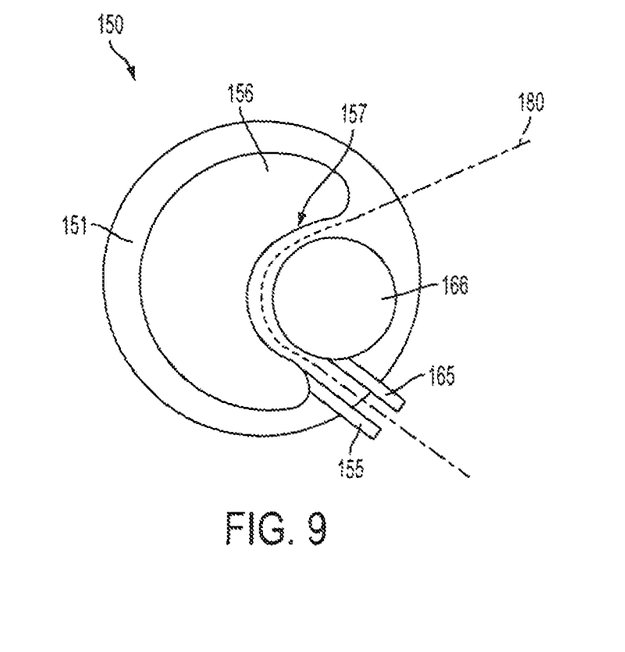
FIG. 9 is a top cross-sectional view of a dual reservoir port according to an embodiment of the invention.

To minimize the footprint of the port within the port pocket, a concave reservoir 156 can be configured next to a convex reservoir 166 as shown in the port 150 of FIG. 9. The port 150 features a concave aspiration reservoir 156 and a convex infusion reservoir 166 formed into the port body 151. The concave aspiration reservoir 156 is completely contoured to facilitate laminar flow, and has a side wall 157 which provides space in the port body 151 for a convex infusion reservoir 166. The outlet stems 155, 165 can be positioned tangentially to reservoir walls. Since the concave side wall 157 and the infusion reservoir 166 approximate the same curve 180, the footprint of the port 150 can be minimized. Further, the contour side walls according to the present embodiment maintain optimal port characteristics including high flow rates, laminar flow, and a minimized footprint within the port pocket. The shapes can be formed in port bodies made of plastics or metals using methods known in the art, including injection molding or drilling techniques. Since the septa will also assume unique shapes and sizes, medical professionals can palpate septa and/or retaining rings to differentiate between aspiration and infusion reservoirs once the port is implanted subcutaneously. Additional palpative features can be added to surfaces such as the port body, septum or retaining rings for differentiating aspiration and infusion reservoirs.

Figure 10:
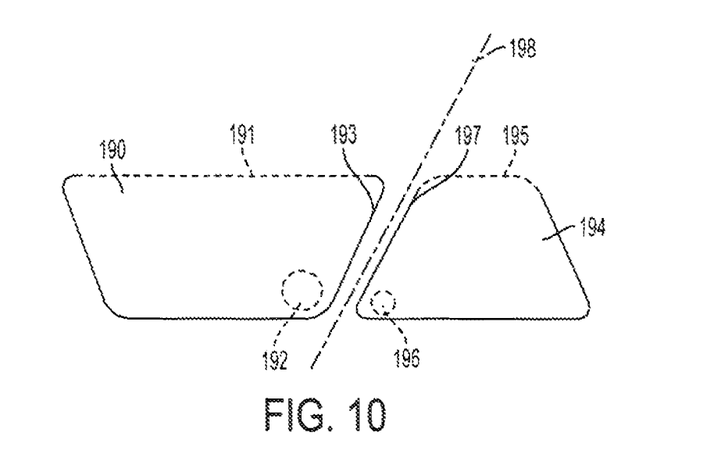
FIG. 10 is a cross-sectional view of funnel shaped reservoirs according to an embodiment of the invention.

Since reservoirs are dedicated for aspiration and infusion, reservoir side walls can be funnel-shaped to optimize flushing action, as shown in the reservoir profiles of FIG. 10. The aspiration reservoir 190 is defined by side walls 193 that taper in the direction away from the bottom surface of an aspiration reservoir septum 191. An outlet lumen 192 is positioned substantially tangential to a side wall 193 of the reservoir 190. Since the reservoir 190 takes on the shape of a funnel that opens up, as fluid is aspirated up through a needle, upward flow into the needle opening will be facilitated, optimizing the movement of fluid out of the reservoir. The infusion reservoir 194 is defined by side walls 197 that taper in the direction towards the bottom surface of the infusion reservoir septum 195. An outlet lumen 196 is substantially tangential to a side wall 197 of the reservoir 194. Since the reservoir 194 takes on a funnel shape that opens down, as fluid is infused down into the reservoir 194 through a needle, the flow of fluid downward and through to the outlet lumen 196 will be facilitated, providing a better flushing action within the reservoir 194. Clearing fluid out of the reservoirs decreases the incidence of sludge, which can impair device performance and lead to increased infection rates. Port reservoirs with funnel shapes can be manufactured using port body manufacturing techniques known in the art, including injection molding and drilling techniques. A further advantage of ports according to this embodiment is that side walls 193, 197 can be designed to slant such that they approximate the same curve 198, decreasing the total footprint of the port. However, embodiments of the invention are not limited to multi-reservoir ports sharing an integral body, and performance advantages of the invention can be maintained where reservoirs are formed from separate bodies and implanted at separate locations within the body.

A needle set 300 optimized for use with the port systems described above is shown in FIG. 11 according to an embodiment of the invention. The needle set 300 includes an aspiration needle 302 having a proximal 301 and distal 305 end, and an infusion needle 304 having a proximal 303 and distal 307 end. Each needle has a lumen extending from proximal to distal ends, terminating at an opening in the distal tip. The gauge of each needle shaft can be equal or customized based on desired flow rates. The needle tip configurations can also be customized based on desired fluid dynamic characteristics. For instance, the aspiration needle can be used with a trocar for providing a needle opening facing downward, while the infusion needle can be a Huber type design, having a needle opening facing the side. The aspiration needle 302 is in fluid communication with an aspiration extension tube 312 and the infusion needle 304 is in fluid communication with an infusion extension tube 314. Each extension tube 312, 314 has a connection element 322, 324 for connection to a medical apparatus such as a power injector for performing automated power blood withdrawal and return functions. The needles 302, 304 are connected to and separated by a spacing member 310 such that the spacing corresponds to the target stick points in septa of a corresponding port. Spacing between needles 302, 304 can be customized depending on the port it is intended to be compatible with, and provided with a kit including the port or referencing the port model.

Figure 11:
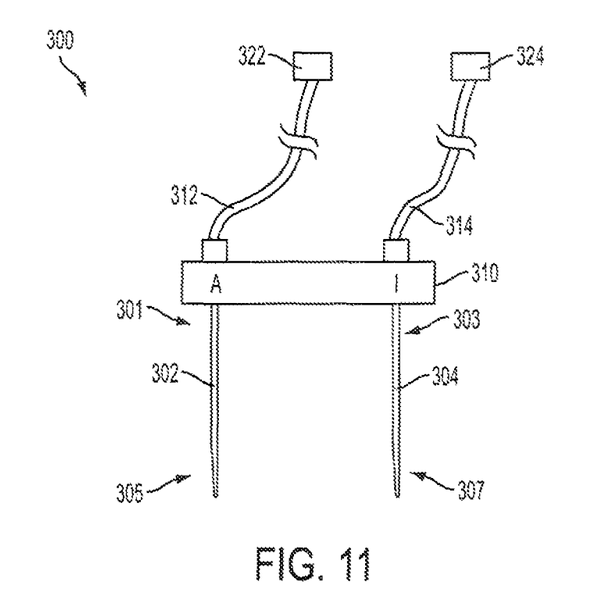
FIG. 11 is a side view of an infusion/aspiration needle assembly according to an embodiment of the invention.
Figure 12:
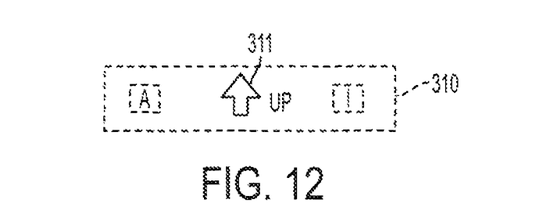
FIG. 12 is a diagram of a top view of the needle assembly shown in FIG. 10 according to an embodiment of the invention.

Since the system is customized by dedicating reservoirs, conduits and catheter tip configurations for aspiration or infusion, it is important that the correct reservoirs be identifiable to the medical professional accessing the port after it is subcutaneously implanted. Markings on the needle set can indicate which side is dedicated for aspiration vs. infusion. This marking can be alphanumeric, such as for example, the "A" (for aspiration) or "I" (for infusion) as shown in FIG. 11. Since the port is always oriented with the outlet stems 55, 65 pointing in the superior or up direction (as illustrated in FIG. 1), ports according to the present invention could be manufactured with a specification requiring that the aspiration reservoir be on the outside or right position relative to the body, and the infusion reservoir be on the left or inside. In addition, a symbolic marking can be placed on the top of the spacing member as shown in FIG. 12, where an arrow indicates which direction is superior or up. Further, aspiration and infusion needles can be independent, without being linked to a spacing member. For instance, first and second needles can be separately included in a needle kit. The first needle can be marked "A" which can be used for aspiration, while a separate second needle included in the same kit can be marked "I" and can be used for infusion.

Figure 13:
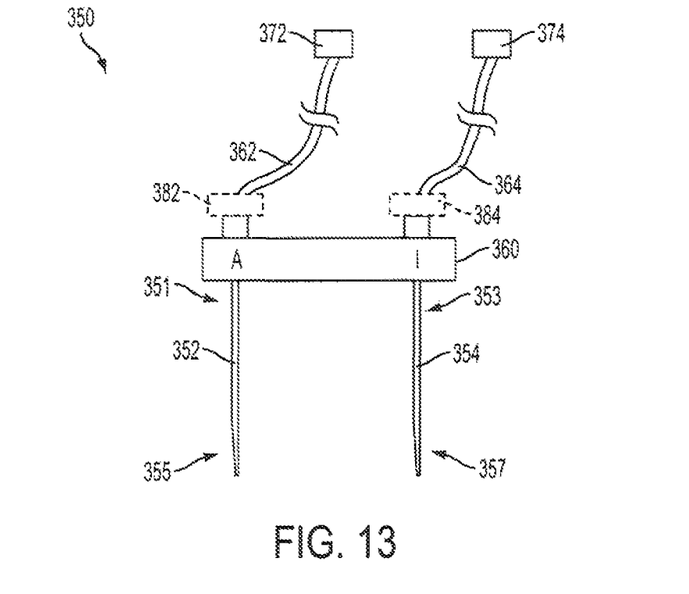
FIG. 13 is a side view of a needle assembly according to an embodiment of the invention.

As mentioned above, once ports according to the invention are implanted subcutaneously, it is critical that the medical professional accessing the port properly distinguish between aspiration and infusion reservoirs. A needle set 350 as illustrated in FIG. 13 includes measurement components 382, 384 corresponding to the aspiration 352 and infusion 354 needles for determining needle access in the proper reservoir. The needle set 350 includes an aspiration needle 352 having a proximal 351 and distal 355 end, and an infusion needle 354 having a proximal 353 and distal 357 end. The aspiration needle 352 is in fluid communication with an aspiration extension tube 362 and the infusion needle 354 is in fluid communication with an infusion extension tube 364. The needles 352, 354 are connected to and separated by a spacing member 360. Each extension tube 362, 364 has a connection element 372, 374 for connection to a medical apparatus such as a power injector for performing automated power blood withdrawal and return. Each needle is operably connected to one or a combination of measurement components 382, 384, which may include a pressure transducer, a flow rate meter or an ECG electrode.

Each measurement component can be used individually or in combination with other components to indicate whether or not the correct reservoir has been accessed. Once the aspiration 352 and infusion 354 needles puncture their respective septa and are in fluid communication with aspiration and infusion reservoirs, a fluid such as saline can be introduced as a medium to propagate the value being measured. The relationship between these measured properties is summarized in FIG. 14. If pressure transducers are used as the measurement components 382, 384, a fluid such as saline can be infused at equivalent flow rates into each reservoir. If the needles are in fluid communication with the correct reservoirs, the pressure measured at the infusion measurement component 384 will be greater than the pressure measured at the aspiration measurement component 382 since the cross-sectional area of the infusion channels are less than the cross-sectional area of the aspiration channels. Relative pressure levels can therefore be used to indicate whether a needle is accessing the aspiration or infusion reservoir. If flow rate monitors are used as the measurement components 382, 384, a fluid such as saline can be infused at equivalent pressures into each reservoir. If the needles are in fluid communication with the correct reservoirs, the flow rate measured at the infusion measurement component 384 will be less than the flow rate measured at the aspiration measurement component 382 since the infusion channels have a smaller cross-sectional area than the aspiration channels. Thus relative flow rates can also indicate whether a needle is accessing the correct reservoir. As an alternative to using a flow rate monitor, gravity bags can be connected to each reservoir, and the drop in fluid levels in each bag can be observed over a period of time, indicating which reservoir had the higher flow rate.

Figure 14:
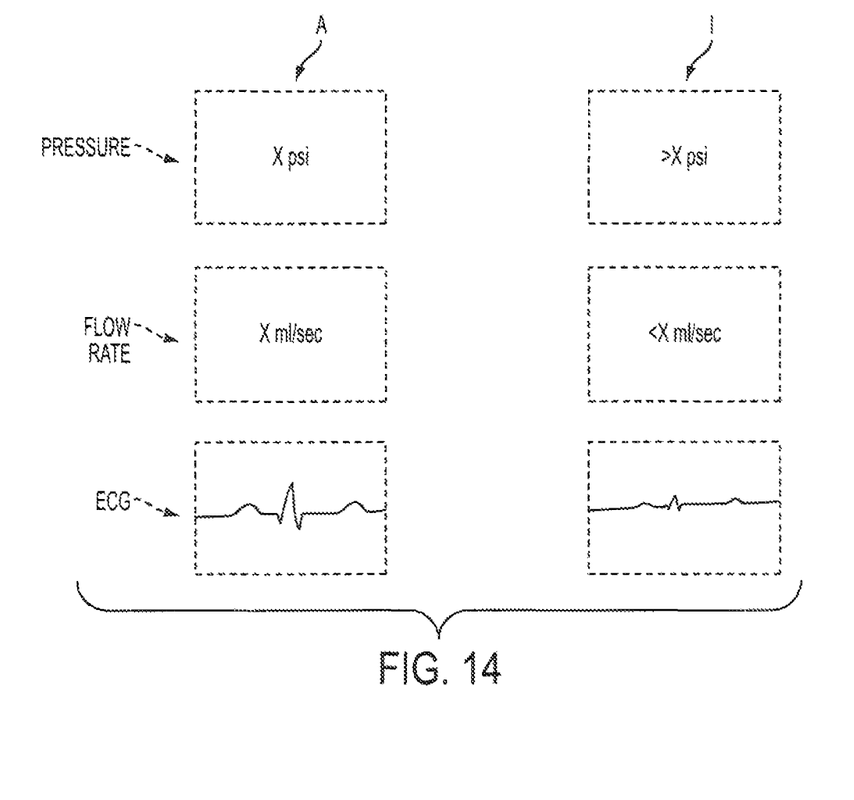
FIG. 14 is a diagram of relative pressures, flow rates, and ECG waveforms between aspiration and infusion channels according to an embodiment of the invention.

ECG electrodes can also be used as the measurement components 382, 384 for detecting an ECG signal. A column of saline can be introduced into each of the aspiration and infusion channels, providing a conductive pathway for detecting an ECG signal. As shown in FIG. 1, since the tip of the catheter terminates near the junction of the superior vena cava and the right atrium, the electrical signals generated in the heart from the SA node can propagate from the tip of the catheter to the ECG electrodes operating as measurement components 382, 384. As illustrated in FIG. 14, the column of saline on the infusion side propagates a dampened ECG waveform relative to the column of saline on the aspiration side. Since the infusion side holds a narrower column of saline relative to the aspiration side, the infusion ECG waveform will appear dampened relative to the aspiration ECG waveform. Signal processing techniques known in the art can be used to calculate relative amplitudes or energy levels of each waveform for determining which reservoir a needle has accessed.

Alternative methods could be used for subcutaneous identification of aspiration and infusion ports. For instance, a radiopaque alphanumeric such as "I" for infusion and "A" for aspiration could be disposed on a port component using techniques known in the art, alternatively, symbols such as "+" for infusion and "−" for aspiration can be used as well. The bottom of a port reservoir could also have a deflective surface that deflects the needle upon advancement into the reservoir, providing tactile feedback to the user. For instance, the deflective surface could take a V shape, deflecting the needle towards the center, or an A-frame shape, deflecting the needle away from the center, for indicating that the port is either an aspiration or infusion port.

Treatment according to systems the present invention can vary depending on a number of factors related to patient anatomy and health risks, and the type of treatment being administered. Generally, once the appropriate site for port placement is selected, catheter length should be determined using a pre-insertion measurement technique. Since catheters according to the present invention may use offset or step tip configurations, excess catheter should be squarely cut from the proximal end of the catheter. An incision is made at the site of port implantation, and a subcutaneous port pocket is created to accommodate the port. Since certain embodiments according to the present invention may utilize port reservoirs implanted in different subcutaneous pockets, creation of more than one subcutaneous port pocket may be required. The port is placed in the pocket and the catheter is advanced to its target location. The catheter can be connected to the port at varying points in the implantation process, but visual markers as described above can be used to guide the medical professional regarding which catheter lumen corresponds with a particular outlet stem. When the port is connected and secured within the port pocket, the incision can be closed. The port can be accessed using needle assemblies and techniques as described above. Aspiration and infusion needles can be connected to machine tubing according to markings on connectors and/or the needle assembly, and the machine can be activated to perform the extracorporeal treatment of blood.

What is claimed is:

1. A method comprising:
    delivering a fluid through a port and a catheter, the port comprising:
        a first reservoir comprising a first outlet lumen;
        a second reservoir comprising a second outlet lumen;
        wherein the first reservoir is configured to be larger than the second reservoir, and
        wherein a first cross-sectional area of the first outlet lumen is greater than a second cross-sectional area of the second outlet lumen; and the catheter comprising:
        a first catheter lumen and a second catheter lumen;
        wherein the first catheter lumen has a greater cross-sectional area than the second catheter lumen;
    aspirating the fluid through the first catheter lumen;
    infusing the fluid through the second catheter lumen.

2. The method of claim 1, wherein the first catheter lumen extends between a first catheter lumen proximal opening and a first catheter lumen distal opening.

3. The method of claim 2, wherein the second catheter lumen extending between a second catheter lumen proximal opening and a second catheter lumen distal opening.

4. The method of claim 3, wherein the first catheter lumen distal opening terminates offset from the second catheter lumen distal opening.

* * * * *